United States Patent [19]

Saunders

[11] Patent Number: 5,489,386
[45] Date of Patent: Feb. 6, 1996

[54] DENSITY GRADIENT MEDIUM FOR THE SEPARATION OF CELLS

[75] Inventor: Alexander M. Saunders, San Carlos, Calif.

[73] Assignee: Applied Imaging, Santa Clara, Calif.

[21] Appl. No.: 189,509

[22] Filed: Jan. 31, 1994

[51] Int. Cl.$^6$ .............................. A01N 1/02; B01D 21/26
[52] U.S. Cl. ........................ 210/514; 210/518; 210/782; 210/789; 252/1; 422/101; 435/2
[58] Field of Search ................................ 210/514, 516, 210/518, 782, 789; 422/101; 435/2; 252/1

[56] References Cited

U.S. PATENT DOCUMENTS

| | | | |
|---|---|---|---|
| 4,083,784 | 4/1978 | Zine, Jr. | 210/516 |
| 4,101,422 | 7/1978 | Lamont et al. | 210/84 |
| 4,386,003 | 5/1983 | Fiehler | 210/516 |
| 4,416,778 | 11/1983 | Rogers | 210/516 |
| 4,797,475 | 1/1989 | Terasaki et al. | 514/2 |
| 4,818,418 | 4/1989 | Saunders | 210/782 |
| 4,835,097 | 5/1989 | Saunders | 435/4 |
| 4,917,801 | 4/1990 | Luderer et al. | 210/516 |
| 4,927,750 | 5/1990 | Dorn | 435/2 |
| 5,053,134 | 10/1991 | Luderer et al. | 210/516 |
| 5,169,543 | 12/1992 | Shibata | 210/516 |
| 5,260,186 | 11/1993 | Cercek et al. | 435/2 |
| 5,275,933 | 1/1994 | Teng et al. | 435/2 |

FOREIGN PATENT DOCUMENTS

| | | |
|---|---|---|
| 9107660 | 5/1991 | WIPO . |
| 9116452 | 10/1991 | WIPO . |
| WO93/23754 | 11/1993 | WIPO . |

OTHER PUBLICATIONS

Betke, "Cytological Differentiation of Haemoglobin," 1968, *Bibl. Haemat.*, 29:1085–1093.

Holzgreve, et al., "Detection of fetal DNA in maternal blood by PCR," *The Lancet*, 335:1220–1221 (1990).

Kleihauer, et al., "Demonstration von fetalem hamoglobin in den erythrocyten eines blutausstrichs," *Klin. Wschr.*, 35:43–44 (1957).

Walle, et al., "A Simple Density Gradient for Enriching Subfractions of Solid Tumor Cells," 1983, *Cytometry*, 3(6):402–407.

Bhat, et al., "One–Step Enrichment of Nucleated Red Blood Cells," Journal of Immun. Methods, 158 (1993) pp. 277–280.

Ganshirt–Ahlert, et al., "Magnetic Cell Sorting and the Transferrin Receptor as Potential Means of Prenatal Diagnosis From Maternal Blood," Am.J.Obstet.Gynecol., May 1992, pp. 1350–1355.

Saunders, "Retrospective Time–Resolved Testing: Model I—Time–Resolved Glycohemoglobin," Clinical Chemistry, 37, 1531 (1991).

Hartmann, et al., "The Influence of Chlorpromazine on the Potential–Induced Shape Change of Human Erythrocyte," Bio–Science Reports, vol. 11, No. 4, 1991, pp. 213–221.

Nakashima, et al., "Glycated Hemoglobin in Fractionated Erythrocytes," Clin. Chem., 35/6, 958–962 (1989).

Ihalamulla, et al., "Plasmodium Vivax: Isolation of Mature Asexual Stages and Gametocytes From Infected Human Blood by . . . " Trans. Royal Society of Trop. Med. & Hygiene, 1987, 81, 25–28.

Gadol, et al., "A New Method for Separating Mononuclear Cells from Whole Blood," Diagnostic Immunology, 3:145–154 (1985).

Vincent, et al., "Adjustment of the Osmolality of Percoll for the Isopycnic Separation of Cells and Cell Organelles," Analytical Biochemistry, 141, 322–328 (1984).

(List continued on next page.)

*Primary Examiner*—John Kim
*Attorney, Agent, or Firm*—Townsend & Townsend & Crew

[57] ABSTRACT

A density gradient medium for the isolation and enrichment of rare cells, including fetal nucleated erythrocytes from a peripheral blood sample is described. The medium comprises a colloidal density gradient medium dispersed in a meltable gel. In one aspect of the invention, the density gradient medium is hypertonic to facilitate separation of maternal red blood cells from fetal blood cells.

13 Claims, 2 Drawing Sheets

OTHER PUBLICATIONS

Rennie, et al., "Human Erythrocyte Fractionation in 'Percoll' Density Gradients," Clinica Chimica Acta, 98 (1979) 119–125.

Boyer, et al., "Enrichment of Erythrocytes of Fetal Origin From Adult–Fetal Blood Mixtures via Selective Hemolysis of Adult . . . " Blood, vol. 47, No. 6, Jun. 1976 pp. 883–897.

Wolff, "The Separation of Cells and Subcellular Particles by Particles by Colloidal Silica Density Gradient Centrifugation," Methods in Cell Biology, Chapter 5, 1975, pp. 85–104.

Boyum, "Isolation of Leucocytes from Human Blood Further Observations," Scand. J. Chi. Lab. Invest., 21 (Suppl. 97), (1968) pp. 31–50.

Borun, et al., "The Distribution of $FE^{59}$ Tagged Human Erythrocytes in Centrifuged Specimens as a Function of Cell Age," J. Clin. Invest., vol. 36, 1957, pp. 676–679.

DENSITY GRADIENT MEDIUM FOR THE SEPARATION OF CELLS

This invention relates to a density gradient medium for the separation of cells, and particularly for the separation of blood cells. More particularly, it relates to a meltable gel for use in the isolation of fetal nucleated erythrocytes from maternal cells in a blood sample of a pregnant woman.

BACKGROUND OF THE INVENTION

Fetal tissue, and in particular fetal DNA, is routinely used in prenatal diagnosis and other medical procedures which require an accurate assessment of the genome of the fetus. Currently, the fetal tissue is obtained by the use of amniocentesis, chorionic villus sampling (CVS), fetoscopy, or cordocentesis, as described in Thompson and Thompson *Genetics in Medicine,* 5th Edition, W. B. Saunders Co., Philadelphia, 1991.

In amniocentesis, a sample of amniotic fluid, which contains fetal cells, is transabdominally removed from the mother, with a needle and syringe. Amniocentesis has inherent associated risks. The major risk is induction of miscarriage which is estimated to occur at 1 in 200 amniocenteses. Other risks include maternal infection and physical damage to the fetus. In CVS, fetal trophoblast tissue is aspirated from the villous area of the chorion transcervically or transabdominally. The rate of fetal loss by this method may be as high as 1 in 100. Cordocentesis provides a method of obtaining fetal blood directly from the umbilical cord with ultrasonic guidance. Each of these invasive methods carries risks to both the mother and the fetus.

Although isolation and enrichment of fetal nucleated blood cells from maternal blood has been attempted, the procedure has been very difficult to optimize, primarily due to the rarity of circulating fetal blood cells, and to the biochemical and physiological similarities between fetal blood cells and maternal blood cells.

Accordingly, it would be desirable to have a non-invasive method for isolating and enriching fetal tissue or fetal DNA. It would also be desirable to have a rapid and reliable method of isolating and enriching rare cells from a population of blood cells. Thus, it would be desirable to have a suitable centrifugation medium for the isolation and enrichment of rare cells, including fetal nucleated red blood cells. Surprisingly, the present invention accomplishes these and other related needs.

SUMMARY OF THE INVENTION

The present invention provides a density gradient medium for the separation of cells from a cell population, and particularly for the separation of fetal nucleated erythrocytes from other blood cells.

According to the invention, there is provided a medium for centrifugation of a cell population, the medium comprising a colloid dispersed in a meltable gel, wherein the colloid is capable of maintaining the cell population in a substantially unaggregated state.

According to another aspect of the invention, there is provided a density gradient medium for the density separation of cells in a cell population, the density gradient medium comprising a plurality of layers of a colloid dispersed in a meltable gel, wherein the colloid is capable of maintaining the cell population in a substantially unaggregated state, the layers being enclosed within a vessel having a top and a bottom, the top having an aperture, and wherein the density of the layers increases from the top of the vessel to the bottom of the vessel.

DETAILED DESCRIPTION OF SPECIFIC EMBODIMENTS

Figure 1:
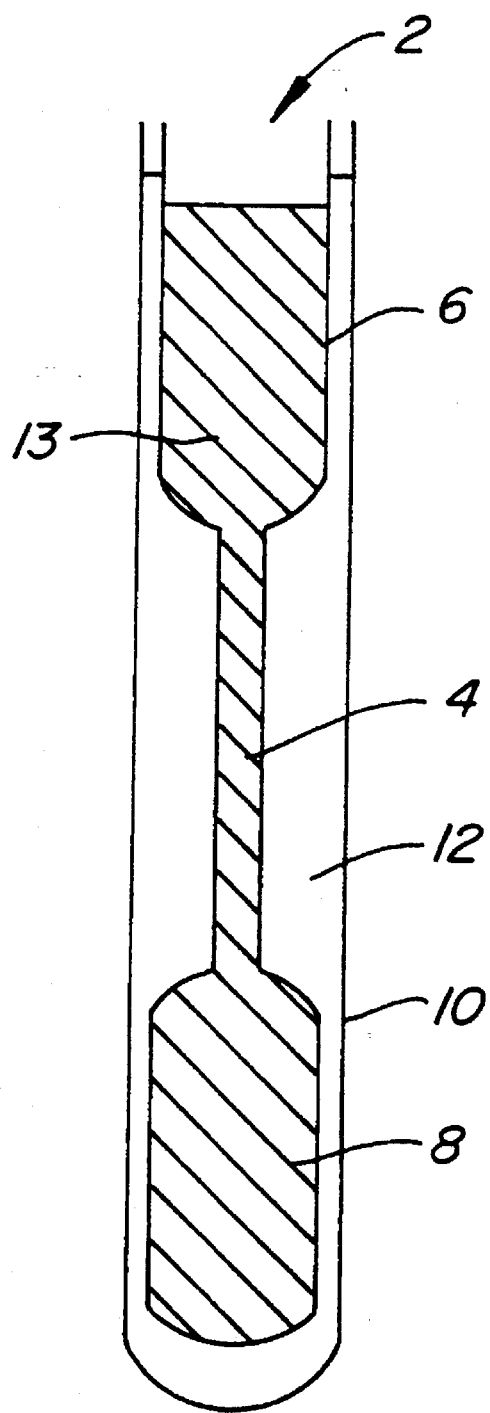
FIG. 1 shows a centrifuge tube of the invention for initial separation of the red blood cell fraction.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, "erythrocytes" or "red blood cells" or "RBC" include adult and fetal red blood cells, and may be nucleated or non-nucleated.

As used herein, "gelatin" means a heterogenous mixture of water soluble proteins of high average molecular weight, typically derived from collagen by hydrolytic action. Suitable forms of gelatin are commercially available, such as from Knox, Sigma Chemical Company, and Aldrich Chemical Company.

As used herein, "tonicity" is the measure of the concentration of a solution relative to cells. For example, an isotonic solution (relative to a blood cell) is one in which the concentrations of solids and salts are similar to those found in nature, such that the cell neither gains nor loses significant amounts of water by osmosis. A hypotonic medium is one in which the salts and solids are of a lower concentration than the cell, such that the cell gains water through osmosis. A hypertonic solution is one in which the salts and solids are of a higher concentration than the cell, such that the cell loses water through osmosis.

Adult red blood cells have an average life span of 120 days. During the 120 days, the cells accumulate irreversible changes, for example in hemoglobin glycosylation. Loss of water without change in solid mass leads to a steadily increasing density with RBC age, as described in U.S. Pat. No. 4,835,097 and in Borun, *J. Clin. Invest.* (1957) 36: 676–679.

Fetal blood cells are rare cells circulating in the maternal blood stream. Fetal cells are believed to "leak" into the maternal blood stream through the placenta. Estimates of the frequency of this rare event vary, but have been reported as approximately 1 in $10^8$ to 1 in $10^{11}$ cells. Holzgreve, W. et al., *Lancet* (1990) 335:1220–1221. During the early period of gestation, fetal red blood cells may be nucleated. Thus, unlike non-nucleated fetal erythrocytes, they contain fetal DNA and may be used for genetic analysis of the fetus without the necessity of invasive procedures.

Methods for isolation of blood cells have been described which use density gradients containing cell aggregating or clumping agents such as methylcellulose, Isopaque™, dextran and Ficoll™, as described in Boyum, *Scand. J. Clin. Lab. Invest.* (1968) 21 (Suppl.97) 31–50, and in Bhat, *N.M.J. Immunol. Meth* (1993) 158:277–280. Isopaque™ is a sodium N-methyl-3,5,-diacetamino-2,4,6-triiodobenzoate, as described in Boyum, supra. Ficoll™ (Accurate Chemical and Scientific Corporation, Westbury, N.Y.) is a synthetic high polymer made by the copolymerization of sucrose and epichlorohydrin. The molecules have a branched structure with a high content of hydroxyl groups giving solubility in aqueous media. Many of these agents are freely diffusible. These agents cause erythrocyte clumping, and thus provide methods for isolating leukocytes from red blood cells. However, under these cell-aggregating conditions, fetal nucleated red blood cells may become physically trapped within a clump of aggregated maternal red blood cells, and therefore will sediment with maternal erythrocytes, as the average density of the clump determines its sedimentation characteristics.

Percoll density gradients have been described in Rennie et al *Clinica Chemica Acta* (1979) 98:119–125, and in Vincent and Nadeau, *Anal. Biochem.* (1984) 141: 322–328. In the Rennie study, an isotonic Percoll density gradient was used to age-fractionate erythrocytes. Leukocytes (white blood cells) were removed prior to the centrifugation process, as they co-fractionated with erythrocytes in isotonic gradient conditions. Thus, removal of leukocytes for use in the Rennie method required an additional time-consuming step.

Initial attempts to characterize fetal cells exploited the fact that maternal cells contain no Y-chromosomes, and thus cells containing Y-specific DNA should be of fetal origin. However, this technique is not available where the fetus is female and thus has limited practicality.

Fetal RBC's differ from maternal RBC's in various ways, including the chemical structure of the hemoglobin contained, the presence and activity of various enzymes such as carbonic anhydrase, and their cell surface antigens. The general size and hemoglobin content of fetal and maternal cells is also different. Thus, when RBC age and lose water and become more dense, the youngest of maternal cells, and the youngest fetal cells, i.e. nucleated fetal RBC's, may have very different densities. Saunders A. M. *Clinical Chemistry* (1991) 157: 1531.

Attempts to isolate fetal red blood cells from maternal blood are described in U.S. Pat. No. 4,416,778. These techniques are cumbersome, time-consuming, expensive, and difficult to adapt to large scale screening or clinical testing applications.

More recent techniques have focussed on biochemical differences between the maternal and fetal cells, for example, cell surface antigens. Bianchi et al (PCT International Application No. PCT/US90/06623) describes a method for enriching fetal nucleated red blood cells from a peripheral blood sample, by the use of an antibody which binds an antigen present on the cell surface of the fetal cells. By appropriately labelling the antibody, the fetal cell/antibody complexes may be sorted from the maternal cells using flow cytometry such as fluorescence-activated cell sorting (FACS), or by using magnetic active cell separation (MACS).

Similarly, Ganshert-Ahlert et al, *Am. J. Obstet. Gynecol.* (1992) 1350–1355 and PCT Publication WO 9323754, describes a complicated method of enriching for fetal nucleated erythrocytes using a triple density gradient on whole maternal blood, followed by use of the transferrin receptor to enrich fetal nucleated red blood cells. A flow cytometry or magnetic separation step is then required to identify the labelled cells. As noted in the Ganshert-Ahlert reference, the use of the transferrin receptor still does not provide a reliable identification of fetal cells in a circulating maternal cell population. Further, this enrichment protocol requires expensive reagents and lengthy laboratory procedures, and is thus unacceptable in many commercial or large-scale screening and diagnostic applications.

The present invention provides an economical density gradient medium for use in centrifugation of cell samples, and particularly for use in enriching rare cells from a population of blood cells, and more particularly useful for enriching fetal nucleated red blood cells from a maternal blood cell population.

In one embodiment of the invention, the density gradient medium may be used to isolate and enrich fetal nucleated red blood cells cells from a sample of peripheral maternal blood, as described in copending U.S. application Ser. No. 08/190, 327 which is incorporated by reference. A first centrifuge step provides an initial enrichment which separates the low density red blood cell fraction and all the white blood cells from the more dense red blood cells, and from the serum and serum proteins. Preferably, the first centrifuge tube of the invention is made of soft plastic, in order to facilitate the movement of the blood cells through the tube. Suitable tubes are described in copending U.S. patent application Ser. No. 08/189,249. Plastic hourglass shaped tubes are preferably supported within the centrifuge, to prevent excessive deformity or collapse of the tube at the narrow central channel portions. Support may be provided by any suitable means. For example, a solid removable support cast may be wrapped around the tube. In a preferred embodiment of the invention, the tube is supported in a liquid support medium within a larger vessel, such as a test tube, as described in copending U.S. patent application Ser. No. 08/189,249. The level of liquid is at least high enough to cover the narrow portion of the tube. Preferably, the weight of the volume of the liquid support medium displaced by the sample tube is approximately equivalent to the weight of the volume of the sample tube and its contents. A preferred liquid support medium for use in the invention is water.

A preferred centrifuge tube of the present invention is shown in FIG. 1. The tube (2) of FIG. 1 is hourglass shaped, comprising a narrowed central channel (4), together with larger upper (6) and lower (8) chambers. The tube is housed within an outer vessel (10), which contains a liquid support medium (12), for example water, at a level sufficient to immerse the narrowed portion of the hourglass shaped tube, and preferably at a level equal to that of the sample during centrifugation. The tube may be precalibrated, such that for a blood sample (13) of a given volume, and at a set centrifuge spin speed and time, the desired fraction is isolated in the narrow channel of the tube, which widens the band, thus greatly facilitating the harvesting of the desired red blood cell fraction.

The centrifugation medium in the first centrifuge step is preferably made slightly hypotonic by the addition of water in an amount sufficient to increase the comparative density of fetal and maternal erythrocytes, and to increase the movement of the cells relative to each other, but not of sufficient hypotonicity to provoke cell lysis. Preferably, water is added in an amount between 20 and 30% of the whole blood volume. More preferably, water is added in an amount approximately equal to 25% of the whole blood volume. In some applications, an anti-coagulant may be present in the blood, or may be added prior to the first centrifugation.

A further addition prior to centrifugation in some applications is a small portion of a high density acqueous medium calculated to raise the density of the plasma from 1.025 to 1.035 gm/ml. In one aspect of the invention, compounds which permit red blood cell deformation are added to the blood sample in the first centrifuge tube, in order to provide additional cell deformity and increased movement of the cells relative to each other. Suitable red blood cell deforming compounds are known to those of skill in the art. A preferred red cell deforming compound is chlorpromazine (2-chloro-N,N-dimethyl-10H-phenothiazine-10-propanamine) as described in Hartmann and Glaser, *Bioscience Reports* (1991) 11:4 213–221.

The first centrifugation step of the present invention comprises a series of increasing spin speeds. The speeds may be adjusted manually during the course of the centrifugation step, or preferably, may be pre-programmed into a suitable automated centrifuge.

The first centrifugation is preferably conducted at plurality of increasing speeds, rather than a single high speed spin. This gradual approach provides a finer separation by density than may be achieved in single high speed bulk separation steps.

In the first centrifugation step, the whole blood fraction is initially spun at low speed to bring cells away from the plasma, thus providing an initial contribution to cell separation. The tube is then spun at one or more intermediate speeds to permit movement of the cells relative to each other, and to achieve equilibrium density of the cells relative to each other. At the highest speeds, the cells are also packed in their equilibrium density positions to create a blood cell stack and to facilitate recovery of the red blood cell layer after centrifugation.

In a preferred embodiment of the present invention, the first spin occurs at less than 200 g for five minutes, followed by a spin in the range of 2500–3000 g for fifteen minutes, with a high speed spin at approximately 14,000 g for five minutes. One of skill in the art would recognize that optimization of centrifugation speeds and durations depends on factors including the volume of blood sample, the type, shape, and height-to-width ratio of the centrifuge tube, the tonicity of the medium and the density modified plasma, and the presence or absence of blood cell deforming compounds. Optimization of these conditions is within the purview of the skilled artisan.

After the first centrifugation step, a fraction containing the red blood cells is obtained. This fraction also includes the white blood cells. The top of the tube contains the plasma fraction. The nucleated red blood cells, which are more dense than plasma but less dense than other red blood cells, will fractionate at the top of the red blood cell stack found just below the plasma and will be variably mixed with white blood cells. The use of a precalibrated first centrifuge tube permits easy extraction of the relevant fraction from the narrow portion of the first tube, thus minimizing inclusion of other blood fractions, including serum and plasma from the first centrifugation step.

The fraction containing the red blood cells and white blood cells may be hemolyzed to differentially disrupt the maternal red blood cells. Differential hemolysis of the maternal red blood cells permits the destruction of a significant number of the remaining maternal red blood cells while preserving the majority of the fetal-origin cells, Boyer S. H. et al, *Blood* (1976) 47(6): 883–897. The differential hemolysis may occur in any suitable reaction vessel. In a preferred embodiment, the differential hemolysis of the maternal red blood cells occurs in an upper portion of the second centrifugation vessel, such that the hemolysis reaction may be stopped by centrifuging the reaction products, i.e. the preserved red blood cells, into the density gradient medium, thus removing the red blood cells from the hemolysis reagents.

The differential hemolysis according to the invention utilizes the fact that red blood cells may be disrupted in solutions containing $NH_4^-$ and $HCO_3^-$ ions. The cell disruption may be decelerated by inhibitors of the enzyme carbonic anhydrase. Carbonic anhydrase levels are at least five fold higher in adult erythrocytes than in fetal erythrocytes. Thus, the rate of $NH_4$—$HCO_3$ mediated hemolysis is slower for fetal red blood cells, including fetal nucleated red blood cells, than for adult red blood cells, particularly in the presence of carbonic anhydrase inhibitors. Preferred carbonic anhydrase inhibitors for use in the invention include acetazolamide, ethoxzolamide (6-ethoxyzolamide, Sigma Chemical Co.) and methoxzolamide.

Differential hemolysis results in a population of white blood cells together with red blood cells enriched for fetal red blood cells. According to the present invention, the level of enrichment of fetal cells after the hemolysis is at least one thousand fold. The enriched fetal red blood cell fraction is then centrifuged through the density gradient medium in order to harvest the fraction enriched for fetal nucleated red blood cells, and to remove red blood cell fragments resulting from the hemolysis reaction and the majority of white blood cells. According to the present invention, the fetal nucleated red blood cells present in an initial sample of 20 ml of peripheral blood may be reduced into a 20 microliter sample, thus providing easy identification and analysis on a microscope slide, or by polymerase chain reaction.

The second centrifugation step of the present invention utilizes a density gradient medium. After hemolysis, the nucleated red blood cells are expected to equilibrate in a density gradient at approximately the same density as granulocytes, a component of the white blood cell fraction, as described in PCT Application No. WO 9323754. However, in the present invention, the tonicity and density of the gradient medium allows separation and enrichment of the fetal nucleated erythrocytes from the white blood cell components of the sample.

The density gradient medium for use in the present invention is comprised of a colloid dispersed in a meltable gel. The colloid imparts the required density to the gradient medium. Thus, by altering the concentration of the colloid, the density of the medium may be correspondingly altered. The particulate nature of the colloid enables immobilization of separate layers of density without diffusion of one layer into another while in the gel state. Further, the colloid is capable of maintaining the blood cells in a substantially unaggregated state. As used herein, substantially unaggregated means that the cells are able to move relative to each other according to their densities and the tonicity of the medium, and do not form clumps which trap cells such that the trapped cells are unable to freely migrate through the density gradient medium in accordance with their densities. A preferred colloid which imparts the density to the medium for use in the invention is polyvinyl-pyrrolidone coated silica, for example, Percoll™, manufactured by Pharmacia, and available from Sigma Chemical Co.

The density gradient medium for use in enriching fetal nucleated erythrocytes according to the invention is hypertonic. Under hypertonic conditions, red blood cells shrink and thus become more dense. Under these conditions, white blood cells maintain a constant density. Thus, by selectively shrinking the erythrocytes in a hypertonic medium, the density of these cells increases and they equilibrate within the gradient at a different density from the white blood cells.

The medium may be made hypertonic by the addition of salts to the centrifugation mixture. Suitable salts for use in the invention include sodium chloride, potassium chloride, or lithium chloride, or any mixture thereof. Commercially available balanced salt solution mixtures may also be used, such as Dulbecco's phosphate buffered saline (PBS), Hanks balanced salt solution, Earl's balanced salt solution and the like.

Gels for use in the present invention are meltable gels. As used herein, "meltable" includes any gel capable of transition between a gel state and a sol state. As used herein, "melt" describes the transition from the gel state to the sol state, which may be accomplished by any suitable means, including the application of heat, light, electric current, magnetic or physical disruption, chemical compounds, and the like. In a preferred embodiment of the invention, the meltable gels are converted from the gel state to the sol state by the application of heat. In this embodiment, the gels are preferably in the gel state at room temperature, but are capable of being converted to the sol state at a temperature low enough to maintain the integrity of any cellular components which are in association with the gel. In a most preferred embodiment, the density gradient medium comprising the meltable gel is in the gel state at room temperature, may be converted from the gel state to the sol state at 37° C., and thereafter remains in the sol state at room temperature for a period of sufficient duration to carry out the methods of the present invention.

In another embodiment of the invention, the meltable gel may be converted from the gel state to the sol state by the application of a chemical compound. For example, carrageenin (Sigma Chemical Company, St. Louis Mo.) or aliginic acid (Kelco, San Diego, Calif.) form a gel cross-linked with multivalent cations. Application of a chelating agent, such as EDTA, destroys the cross-linkage of the gel, and melts the gel into the sol state. Chemical chelating agents are known to those of skill in the art and are described in, for example, the Merck Index, 11th Edition.

Non-limiting examples of meltable gels for use in the invention include agar, agarose, low melting point agarose, alginic acid, carrageenan, pectin, or gelatin. A preferred gel for use in the invention is gelatin. It will be appreciated by the person of skill in the art that combinations of these gels may also be used. Preferably, when in the sol form the gel is reasonably transparent, so that the separated fractions may be seen for the purpose of harvesting.

Methods of preparation of the colloid/gel density gradient medium may vary depending on the time for which the gradient is to be stored, the nature of the cells to be separated, and the temperature at which the gel is melted. For example, a gel that has a relatively high melting temperature is typically prepared in a lower concentration than a gel with a low melting temperature.

In a preferred embodiment of the present invention, the density gradient medium is supplied in a second centrifuge tube as a prepackaged unit. Thus, the density gradient may be stored for lengthy periods of time, which eliminates the preparation step in the laboratory. In use, the enriched red blood cell fraction obtained from the first centrifugation step may be transferred directly to the upper portion of the second centrifuge tube, and the hemolysis reaction may take place in that position. The gel may then be melted, and centrifuged such that the reaction products of the hemolysis reaction i.e. the preserved cells are driven into the melted gel. The hypertonicity of the density gradient medium serves to decelerate the hemolysis reaction.

In this embodiment of the invention, the prepackaged density gradient medium may be supplied in kit form together with any one or more of the following additional compounds: hemolysis reagents, red blood cell deforming compounds such as chlorpromazine, precalibrated first step centrifuge tubes, and reagents for control experiments.

In another embodiment of the present invention, the hemolysis reaction may occur in a separate reaction vessel, and the hemolysis reaction may be stopped by the application of chemical compounds, as described above.

The density gradient may optionally include preservatives, which may be in any form suitable for incorporation into the density gradient, such as solid or liquid preservatives. Non-limiting examples of suitable preservatives include azide, propyl p-hydroxybenzoate, and methyl p-hydroxybenzoate.

The density gradient may optionally also include further reagents that affect the cells centrifuged into it, for example a high concentration of carbonic anhydrase inhibitor may be included to completely stop reaction which may cause hemolysis.

Methods for demonstrating successful separation of centrifuged samples and enrichment of fetal nucleated red blood cells are known to those of skill in the art and include actual harvesting of nucleated red blood cells and counting on a solid support such as a prepared slide or a hemocytometer, fluorescent in situ hybridization, and measuring a surrogate for density of each red blood cell or each red blood cell fraction.

In the first method, the enriched cell population may be transferred to a solid support and stained with stains specific for fetal or nuclear material. These methods are known to the person of skill in the art. For example, the Kleihauer-Betke adult hemoglobin extraction as described in Kleihauer E. et al, *Klinicia Wochenschr.* (1957) 35: 43–44, and Betke, K. *Bibl. Haem.* (1968) 29:1085, may be used to extract hemoglobin from any remaining maternal red blood cells, and thus preserve fetal hemoglobin. Then, the cells may be examined for hemoglobin. Alternately, the cells may be examined for the presence of a nucleus, using a nuclear stain known to those of skill in the art. Nuclear stains may recognize chromatin, nuclear proteins, DNA or other nuclear components. Non-limiting examples of nuclear stains include methylene blue, hematoxylin, propidinium iodide, and thionin.

In the latter method, the mean cell volume (MCV) of red blood cells in a subsample or fraction of all red blood cells is such a surrogate. Similarly, the mean cell hemoglobin concentration (MCHC) is another surrogate for measuring the density of red blood cells. Both measurements are available on hemalogs or routine automated hematology devices, e.g. Miles-Technicon's "H" series, including H·1™, H·2™ and H·3™.

By the use of the methods and compositions of the present invention, a population of fetal nucleated erythrocytes may be enriched by a factor of one thousand fold or more, from a starting volume of 20 ml, as exemplified in Table 1. In Table 1, a starting number of fetal nucleated red blood cells expected to be found in a 20 ml sample of maternal peripheral blood was calculated based on estimated "leak" values of between 1 in $10^8$ and 1 in $10^{11}$ cells.

TABLE 1

| Enrichment Step | Volume | Expected NRBC | Observed NRBC |
| --- | --- | --- | --- |
| Starting Volume | 20 ml | 20–100 | |
| After first centrifuge step | 0.5 ml | 20–100 | |
| After second centrifuge step | 0.02 ml (20 μl) | 20–100 | 20 |

In another embodiment of the present invention, rare cells may be separated from a population of blood cells. Detection of the presence or absence of the rare cells may be used for diagnosis or differential diagnosis of disease conditions in which the rare cells are present. Alternatively, the rare cells may be isolated according to the methods of the invention for use in diagnosis or therapy.

In this embodiment of the invention, the method comprises the steps of centrifuging the blood sample in a first centrifugation vessel to obtain a fraction containing the rare cells; transferring the rare cell fraction to an upper portion of a second centrifugation vessel, the second centrifugation vessel having a density gradient medium consisting of a colloid dispersed in a meltable gel, wherein the colloid is capable of maintaining the rare cells in a substantially unaggregated state; melting the gel; and centrifuging the rare cell fraction through the density gradient medium to obtain a fraction enriched in rare cells.

Rare cells may be any cell which exhibit or can be made to exhibit differential density gradient characteristics such as increased or decreased density or altered shape. Thus, these characteristics of rare cells may be manipulated by varying the osmolarity of the environment or the cellular content. Non-limiting examples of rare cells which may be isolated according to the invention include erythrocytes infected with viruses or other infectious agents, erythrocytic infestations including parasitic infestations and trypanosomes, cancerous cells, or abnormally shaped cells such as sickled cells. Known erythrocyte infestations include those associated with malaria parasites *Plasmodium vivax* and *Plasmodium falciparum* as described in Ihalamulla R. L. et al. *Trans. Royal. Soc. of Tropical Medicine and Hygiene* (1987) 81:25–28. Rare cells may include aberrantly shaped cells such as may be found in the thalassemias, sickle cell anemia, and a variety of other hematologic disorders. Rare cells also include adult nucleated red blood cells, which may occur in some disease states, for example, myeloproliferative disorders such as myelofibrosis and polycythemis vera (Vaquez' disease).

Enriched rare cells, including fetal nucleated red blood cells may be used in a variety of ways which are apparent to the skilled artisan. For example, the DNA of fetal nucleated red blood cells may be used in the polymerase chain reaction with appropriate primers to detect the presence or absence of a medical condition, such as a particular disease allele. The cells may be used to create secondary or stable cell lines.

The present invention will be further illustrated by Examples 1 through 5, which are intended to be exemplary and not scope limiting.

EXPERIMENTAL EXAMPLES

EXAMPLE 1

Preparation of sample for first centrifuge step

A first centrifuge tube was prepared as follows. A polyethylene (PE) transfer pipet, E & K #50020 (E & K Scientific, Saratoga, Calif.) having a narrow (1 mm) stem was sealed at the end farthest from the bulb by heat melting the polyethylene until the opening is closed. The bulb was cut transversely to provide a wide opening.

To fill the tube with sample, the sample was placed in the remainder of the cut bulb still attached to the stem. The filled capillary PE was placed into a 10 ml test tube containing 9.5 ml of water, and then placed into a Centra IEC centrifuge model 7. The entire assembly was centrifuged at low g force (138 g) for 5 minutes. This commenced the process of cell separation and dislodged the air block in the capillary.

After the initial centrifugation at 138 g for five minutes, the red blood cells were loosely packed at the lower end. The tube was further centrifuged at 2800 G for 15 minutes, 7000 G for fifteen minutes, and 14,000 G for 5 minutes. The red blood cell stack in the capillary was then cut with a scalpel into 10 equal fragments, each containing red blood cells. The cells from each fragment were resuspended in a medium containing salt and proteins to mimic plasma (0.9% NaCl, 6% bovine serum albumin (BSA)). The cells were prepared for microscopic slide examination to identify fetal nucleated red blood cells or were analyzed for MCV and MCHC.

EXAMPLE 2

Preparation of the Colloid/Gel Density Gradient Medium 10 grams of Knox® gelatin were layered over 50 ml of deionized water and permitted to soak in and swell. The swollen granules of gelatin were then heated to 55° C. until they melted and fused. This was used as the 20% gelatin stock solution. The stock solution may be used immediately or may be stored as a gel at 4° C. and melted before use.

A stock saline solution was prepared from NaCl (4.96 g), KCl (0.76 g), LiCl (0.21 g), $Na_2HPO_4$ (0.67 g), and $KH_2PO_4$ (0.25 g), in 50 ml of deionized water. The stock saline solution had a pH of 6.8, density of 1.085 g/ml, and an osmolarity of 4389.2 mOsm.

Varying density gradient medium solutions of Percoll were made according to the formula:

$$V_0 = V \frac{D - (MS\ DS) - MG\ DG - (1 - MS - MG)}{Do - 1}$$

where
D=desired density
Vo=volume of Percoll added
V=final volume of working solution
Do=density of Percoll stock solution
MS=proportion of stock saline added, calculated from TN/TS
TN=desired tonicity of final solution
TS=measured tonicity of stock salt mix
DS=density of stock saline solution
CG=concentration of stock gelatin as multiple of desired gelatin
MG=proportion of stock gelatin added calculated from 1/CG
DG=density of stock gelatin, and
where $D_O$=1.129 g/ml, DS=1.047 g/ml, TS=4389 mOsm, DG is 1.052 g/ml, and CG is 10× final of 2%.

Density gradient medium solutions (V=100 ml) having densities of 1.110, 1.095, 1.080, and 1.065 g/ml, and having tonicities of 300 (isotonic), 360 (slightly hypertonic), and 500 (strongly hypertonic) mOsm were prepared according the above relationship as follows:

TABLE 2

| DESIRED VALUES | | REQUIRED VOLUMES | | | |
|---|---|---|---|---|---|
| D | Tn | VO | VMS | VMG | Vwater |
| 1.065 | 300 | 43.86 | 6.83 | 10 | 39.3 |
| 1.080 | 300 | 55.49 | 6.83 | 10 | 27.67 |
| 1.095 | 300 | 67.12 | 6.83 | 10 | 16.04 |
| 1.110 | 300 | 78.75 | 6.83 | 10 | 4.41 |
| 1.065 | 360 | 43.36 | 8.2 | 10 | 38.43 |
| 1.080 | 360 | 54.99 | 8.2 | 10 | 26.8 |
| 1.095 | 360 | 66.62 | 8.2 | 10 | 15.17 |
| 1.110 | 360 | 78.25 | 8.2 | 10 | 3.54 |
| 1.065 | 500 | 42.2 | 11.39 | 10 | 36.4 |
| 1.080 | 500 | 53.83 | 11.39 | 10 | 24.77 |
| 1.095 | 500 | 65.46 | 11.39 | 10 | 13.14 |
| 1.110 | 500 | 77.09 | 11.39 | 10 | 1.51 |

The solutions were stable at room temperature for about 1 hour, after which they began to gel.

Gradients were made within a glass 13×100 mm test tube (total volume 9.5 ml) by adding one ml of each 300 mOsm density gradient solution one layer at a time, starting with the most dense and following in descending order.

After each layer was added, the tubes were chilled in ice water. The solutions set in 15–20 minutes, at which time the next solution was added to produce very sharp interfaces. Each tube was sealed and stored at 4° C. until use.

EXAMPLE 3

Figure 2A:
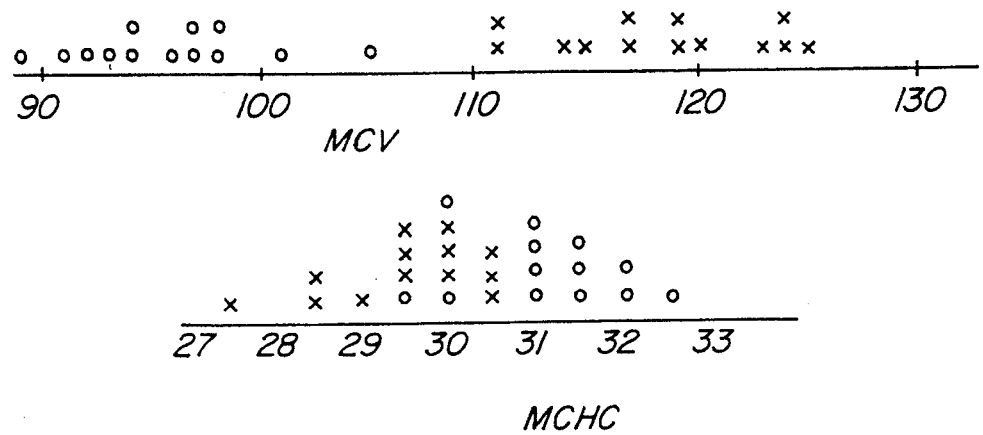
FIG. 2 comprises FIG. 2A and 2B, and is a histogram showing the mean cell volume and the mean cell hemoglobin concentration of umbilical cord blood and maternal blood samples in isotonic (FIG. 2A) and hypotonic (FIG. 2B) conditions.
Figure 2B:
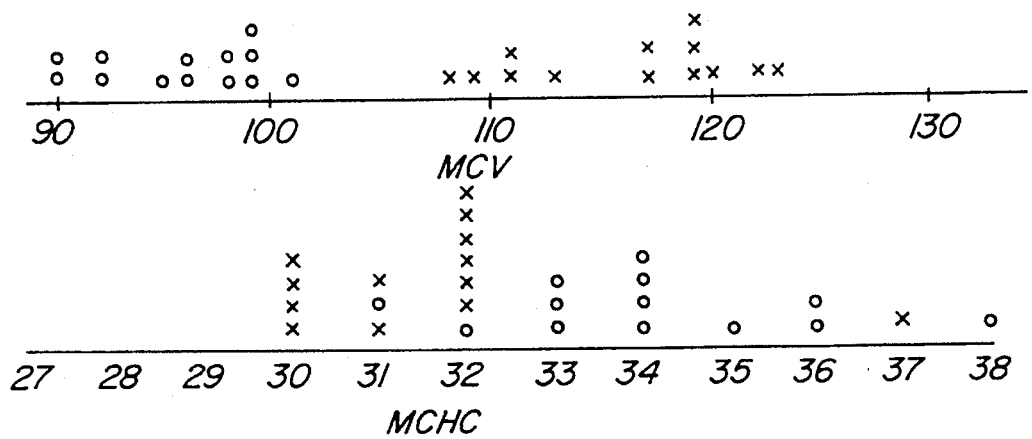

Using whole blood only, the mean cell volume and mean cell hemoglobin concentration of 13 samples was examined before and after a standard addition of water, 25% of volume, to each sample. The results are shown in histogram form in FIG. 2. In FIG. 2, each "X" represents an umbilical cord blood sample, each "O" represents a maternal peripheral blood sample at 12–19 weeks gestation, and "." represents a maternal peripheral blood sample obtained at delivery (40 weeks). The upper panel of FIG. 2 (FIG. 2A) shows the distribution of isotonic whole blood samples, while the lower panel (FIG. 2B) shows the distribution in samples made hypotonic.

It can be seen from FIG. 2 that the mean cell volume of umbilical cord blood samples is well separated from the maternal blood sample mean cell volume, both before and after rendering samples hypotonic. Additionally, there is a marked improvement of separation between maternal cells and cord cells in MCHC measurements after rendering samples hypotonic. Thus, the cell densities as observed by the MCHC measurement, are as great as differences in MCV. However, in non-isotonic conditions, the hemoglobin in each cell does not change, but the larger fetal cells will swell or shrink more than the smaller maternal cells. Thus, a better contrast is observed between MCHC in cord blood samples and maternal samples when the medium is non-isotonic, and facilitates enrichment and isolation of the fetal nucleated erythrocytes in density gradients.

EXAMPLE 4

A hemolyzing mixture of ammonium chloride and sodium bicarbonate at approximately 300 m osmolar salt strength was prepared. Maternal (m) and umbilical cord (c) blood samples were exposed to either a physiological salt solution as a diluent, or the hemolyzing mixture, either in the presence or absence of 30 μl of the carbonic anhydrase inhibitor acetazolamide (at a final concentration of 1 mM),  sodium fluoride (at a final concentration of 150 μm), or azide (1%). The number of intact cells in the final volume of a 15× dilution of blood in the lysis mixture was determined after 7 and after 17 minutes. The results are provided in Tables 3 and 4.

TABLE 3

| Sample | Source | Diluent | Lyse | Inhibitor | 7 min. count | 17 min. count |
|---|---|---|---|---|---|---|
| 1 | M | 280 μl | — | — | 3292 | 3175 |
| 2 | C | 280 | — | — | 4089 | 3922 |
| 3 | M | 30 | 250 | — | 228 | 183 |
| 4 | C | 30 | 250 | — | 760 | 752 |
| 5 | M | | 250 | acetazol-amide | 483 | 213 |
| 6 | C | | 250 | acetazol-amide | 3128 | 2476 |
| 7 | M | | 250 | sodium fluoride | 225 | 218 |
| 8 | C | | 250 | sodium fluoride | 485 | 490 |
| 9 | M | | 250 | azide | 210 | 177 |
| 10 | C | | 250 | azide | 384 | 390 |
| 13 | M | | 250 | acetazol-amide at t = 0 | 389 | 185 |
| 14 | C | | 250 | azide at t = 7 min. | 2301 | 427 |
| 15 | M | 30 μl 10 × PBS | 250 | — | 2704 | 2657 |
| 16 | C | 30 μl 10 × PBS | 250 | — | 4208 | 3958 |

As can be seen from Table 3, cord blood is more resistant to hemolysis when acetazolamide is present in the mixture, while fluoride and azide have little protective effect.

As can be seen from samples 15 and 16, hemolysis is prevented (or cell count is preserved) in a hypertonic medium (samples 15 and 16). This results from a equalization between the extracellular concentration of salt and the intracellular concentration of salt driven by the carbonic anhydrase mediated hemolysis reaction. Thus, the intracellular and extracellular salt concentrations remain stable relative to each other, thus preventing hemolysis.

TABLE 4

| Sample | Source | Diluent | Lyse | Inhibitor | 7 min. count | 17 min. count |
|---|---|---|---|---|---|---|
| 1 | M | 280 μl | — | — | 2921 | 2963 |
| 2 | C | 280 | — | — | 4346 | 4225 |
| 3 | M | 30 | 250 | — | 214 | 216 |
| 4 | C | 30 | 250 | — | 595 | 658 |
| 5 | M | — | 250 | acetazol-amide | 286 | 188 |
| 6 | C | — | 250 | acetazol-amide | 2650 | 2005 |
| 7 | M | 30 μl 10 × PBS at 7 min. | 250 | acetazol-amide | 285 | 303 |
| 8 | C | at 7 min. | 250 | acetazol-amide | 2190 | 2209 |
| 9 | M | 30 μl 10 × NaCl | 250 | — | 2476 | 2456 |
| 10 | C | 30 μl 10 × NaCl | 250 | — | 3433 | 3371 |
| 11 | M | 20 μl 10 × NaCl | 260 | — | 1744 | 1824 |
| 12 | C | 20 μl 10 × NaCl | 270 | — | 2856 | 2646 |
| 13 | M | 10 μl 10 × NaCl | 270 | — | 211 | 169 |
| 14 | C | 10 μl 10 × NaCl | | — | 607 | 419 |

As can be seen from Table 4, salt concentrations above 400 m Osm will prevent lysis of both adult and cord blood samples.

EXAMPLE 5

A blood sample taken from a non-pregnant adult individual was supplemented with umbilical cord blood in amounts of 25%, 12.5%, 8.3%, and 6.25%. The fetal nucleated red blood cells were isolated according to the method of Examples 1 and 2. The final volume obtained after the centrifugation step was 20 µl. The 20 µl volume was divided into 3.5 µl aliquots. For each aliquot, the number of nucleated red blood cells was determined over a standard, constant path on the Wright stained microscope slide of the specimen. The total number of NRBC recovered from each 20 µl volume is shown in Table 5.

TABLE 5

| Sample | NRBC Recovery (# NRBC) |
| --- | --- |
| 25% Cord Blood | 27 |
| 12.5% Cord Blood | 15 |
| 8.3% Cord Blood | 8 |
| 6.25% Cord Blood | 6 |

The data in Table 5 indicate a linear relationship between % of cord blood spiked into a normal blood sample, and the amount of nucleated red blood cells recovered from the sample, indicating the successful enrichment and identification of rare cells according to the methods of the invention.

All publications, patents, and patent applications herein are incorporated by reference to the same extent as if each individual publication or patent application was specifically and individually indicated to be incorporated by reference.

The foregoing description of the preferred embodiments of the present invention has been presented for purposes of illustration and description. They are not intended to be exhaustive or to limit the invention to the precise form disclosed, and many modifications and variations are possible in light of the above teaching, and are intended to be within the scope of the invention.

Although the foregoing invention has been described in some detail by way of illustration and example, for purposes of clarity of understanding, it will be obvious that certain changes and modifications may be practiced within the scope of the appended claims.

What is claimed is:

1. A medium for centrifugation of a cell population, the medium comprising a colloid dispersed in a meltable water-soluble gel, wherein the colloid is capable of maintaining the cell population in a substantially unaggregated state, and wherein the medium comprises a plurality of layers, each layer having a different density.

2. The medium of claim 1, wherein the medium comprises a plurality of layers, each layer having a different density, and wherein the medium is enclosed within a centrifugation vessel having a top and a bottom, the top having an aperture, and wherein the density of the layers increases from the top of the vessel to the bottom of the vessel.

3. The medium of claim 2 additionally comprising a preservative.

4. A medium for centrifugation of a cell population, the medium comprising a colloid dispersed in a meltable water-soluble gel, wherein the colloid is capable of maintaining the cell population in a substantially unaggregated state, and wherein the medium comprises a plurality of layers, each layer having a different density, and wherein the meltable gel is selected from the group consisting of agar, agarose, low melting point agarose, alginic acid, carrageenin, pectin and gelatin.

5. The medium of claim 4, wherein the colloid is polyvinyl-pyrrolidone coated silica.

6. The medium of claim 5, wherein the meltable gel is gelatin.

7. A density gradient medium for the density separation of cells in a cell population, the density gradient medium comprising a plurality of layers of a colloid dispersed in a meltable gel, wherein the colloid is capable of maintaining the cell population in a substantially unaggregated state, the layers being enclosed within a vessel having a top and a bottom, the top having an aperture, and wherein the density of the layers increases from the top of the vessel to the bottom of the vessel.

8. The density gradient medium of claim 7 wherein the cells are fetal nucleated erythrocytes.

9. The density gradient medium of claim 8 wherein the medium is hypertonic relative to the fetal nucleated erythrocytes.

10. The density gradient medium of claim 9 additionally comprising a salt selected from the group consisting of sodium chloride, potassium chloride, phosphate buffered saline, and balanced salt solutions.

11. The density gradient medium of claim 9, wherein the colloid is polyvinyl-pyrrolidone coated silica.

12. A density gradient medium for the density separation of cells in a cell population, the density gradient medium comprising a plurality of layers of a colloid dispersed in a meltable gel, wherein the colloid is capable of maintaining the cell population in a substantially unaggregated state, the layers being enclosed within a vessel having a top and a bottom, the top having an aperture, wherein the density of the layers increases from the top of the vessel to the bottom of the vessel and wherein the meltable gel is selected from the group consisting of agar, agarose, low melting point agarose, alginic acid, carrageenin, pectin and gelatin.

13. The density gradient medium of claim 12, additionally comprising a preservative.

* * * * *